(12) United States Patent
West et al.

(10) Patent No.: US 6,322,541 B2
(45) Date of Patent: *Nov. 27, 2001

(54) VASCULAR INTRODUCER SHEATH AND HEMOSTASIS VALVE FOR USE THEREWITH

(75) Inventors: Ronald L. West, Fort Ann; Mark H. Van Diver, Argyle, both of NY (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/393,865

(22) Filed: Sep. 10, 1999

(51) Int. Cl.[7] .............................. A61M 5/00; A61M 5/14
(52) U.S. Cl. .................... 604/256; 604/167.04; 137/844
(58) Field of Search .................... 604/167.01–167.04, 604/246–247, 256, 523; 251/149.1; 137/844–845, 859

(56) References Cited

U.S. PATENT DOCUMENTS

| | | | |
|---|---|---|---|
| 4,000,739 | 1/1977 | Stevens | 128/214.4 |
| 4,254,773 | 3/1981 | Waldbillig | 128/348 |
| 4,366,817 | 1/1983 | Thomas | 604/174 |
| 4,424,833 | 1/1984 | Spector et al. | 137/849 |
| 4,430,081 | 2/1984 | Timmermans | 604/256 |
| 4,436,519 | 3/1984 | O'Neil | 604/175 |
| 4,798,594 | 1/1989 | Hillstead | 604/167 |
| 4,874,378 | 10/1989 | Hillstead | 604/167 |
| 4,895,565 | 1/1990 | Hillstead | 604/167 |
| 4,929,235 | 5/1990 | Merry et al. | 604/167 |
| 4,944,729 | 7/1990 | Buckberg et al. | 604/164 |
| 4,946,133 | 8/1990 | Johnson et al. | 251/149.1 |
| 4,950,257 | 8/1990 | Hibbs et al. | 604/265 |
| 5,000,745 | 3/1991 | Guest et al. | 604/256 |
| 5,045,065 | 9/1991 | Raulerson | 604/167 |
| 5,059,186 | 10/1991 | Yamamoto et al. | 604/280 |
| 5,092,857 | 3/1992 | Fleischhacker et al. | 604/256 |
| 5,098,393 | 3/1992 | Amplatz et al. | 604/167 |
| 5,114,408 | 5/1992 | Fleischhaker et al. | 604/167 |
| 5,137,519 | 8/1992 | Littrell et al. | 604/174 |
| 5,154,701 | 10/1992 | Cheer et al. | 604/167 |
| 5,167,637 | 12/1992 | Okada et al. | 604/167 |
| 5,188,607 | 2/1993 | Wu | 604/167 |

(List continued on next page.)

FOREIGN PATENT DOCUMENTS

| | | |
|---|---|---|
| 0 369 314 A2 | 5/1990 | (EP) . |
| 0 442 194 A2 | 6/1991 | (EP) . |
| 0 692 278 A1 | 7/1994 | (EP) . |
| WO 99/06099 | 2/1999 | (WO) . |
| WO99/06099 * | 2/1999 | (WO) . |
| WO 99/34849 | 7/1999 | (WO) . |

Primary Examiner—Richard K. Seidel
Assistant Examiner—LoAn H. Thanh
(74) Attorney, Agent, or Firm—Crompton, Seager & Tufte, LLC.

(57) ABSTRACT

A vascular introducer sheath including a tubular shaft and a hemostasis valve assembly connected to the proximal end thereof. The hemostasis valve assembly includes a hub, a cap and a normally-flat gasket disposed therebetween. Both the hub and the cap include continuous curved contact surfaces facing the top and bottom surfaces of the gasket. The continuous contact surfaces may be flat or gently curved and may be smooth or include a means to grip the gasket. At least one of the contact surfaces is formed at an angle to cause the gasket to become convex or concave in response to compression between the hub and the cap. The continuous contact surfaces uniformly distribute forces onto the perimeter of the gasket to avoid stress concentration points that may compromise gasket integrity. In addition, the continuous contact surfaces reduce the amount of pressure necessary to impart the curved shape of the gasket.

22 Claims, 5 Drawing Sheets

U.S. PATENT DOCUMENTS

| | | | |
|---|---|---|---|
| 5,234,410 | 8/1993 | Graham et al. | 604/167 |
| 5,242,410 | 9/1993 | Melker | 604/164 |
| 5,242,413 | 9/1993 | Helliger | 604/167 |
| 5,267,966 | 12/1993 | Paul | 604/167 |
| 5,295,657 | 3/1994 | Atkinson | 251/149 |
| 5,300,033 | 4/1994 | Miller | 604/167 |
| 5,330,435 | 7/1994 | Vaillancourt | 604/167 |
| 5,350,363 | 9/1994 | Goode et al. | 604/167 |
| 5,402,982 | 4/1995 | Atkinson et al. | 251/149 |
| 5,499,975 | 3/1996 | Cope et al. | 604/165 |
| 5,520,655 * | 5/1996 | Davila et al. | |
| 5,520,663 * | 5/1996 | Patterson et al. | |
| 5,538,505 | 7/1996 | Weinstein et al. | 604/167 |
| 5,549,576 | 8/1996 | Patterson et al. | 604/247 |
| 5,613,956 | 3/1997 | Patterson et al. | 604/256 |
| 5,762,630 | 6/1998 | Bley et al. | 604/164 |
| 5,807,350 * | 9/1998 | Diaz. | |
| 5,843,031 | 12/1998 | Hermann et al. | 604/95 |
| 5,911,710 | 6/1999 | Barry et al. | 604/249 |
| 5,944,697 | 8/1999 | Biche | 604/174 |

\* cited by examiner

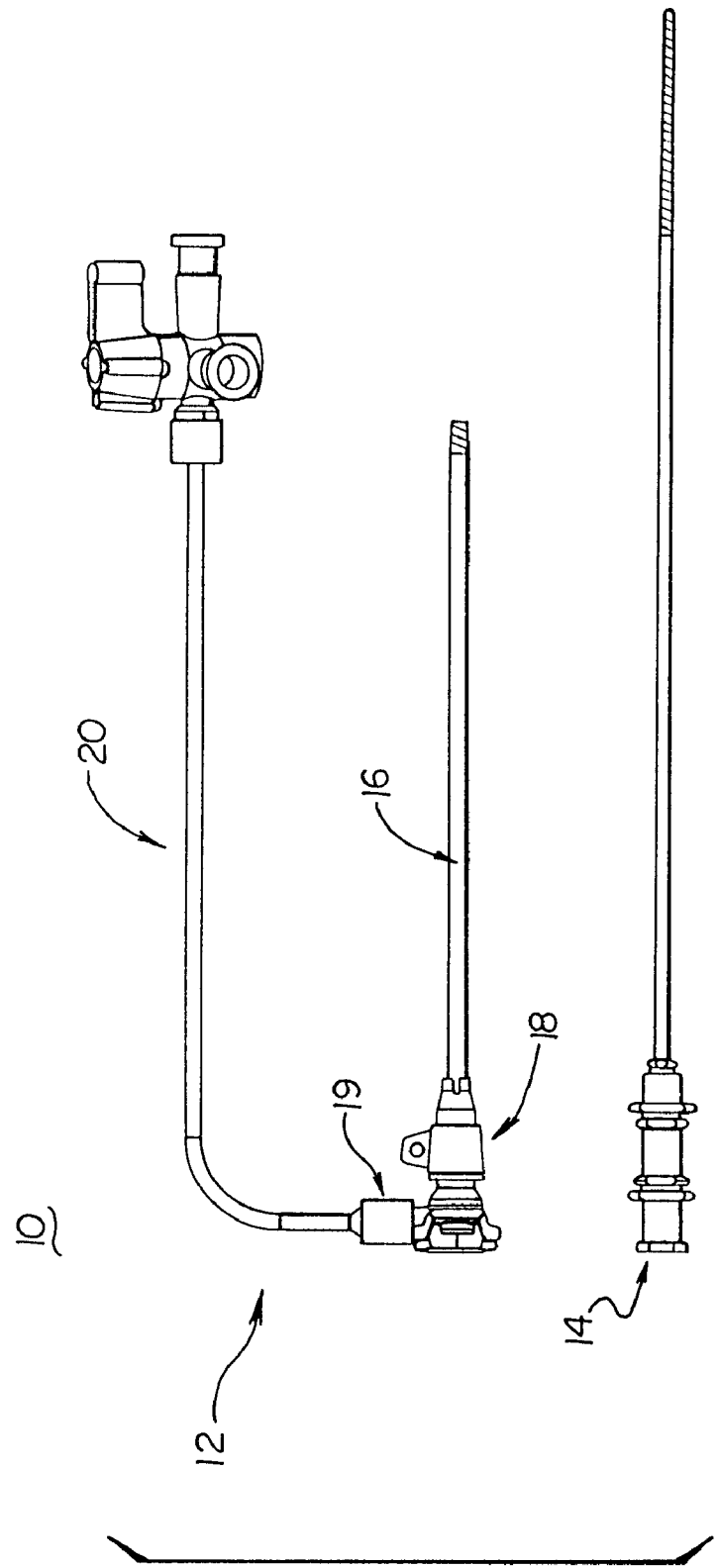

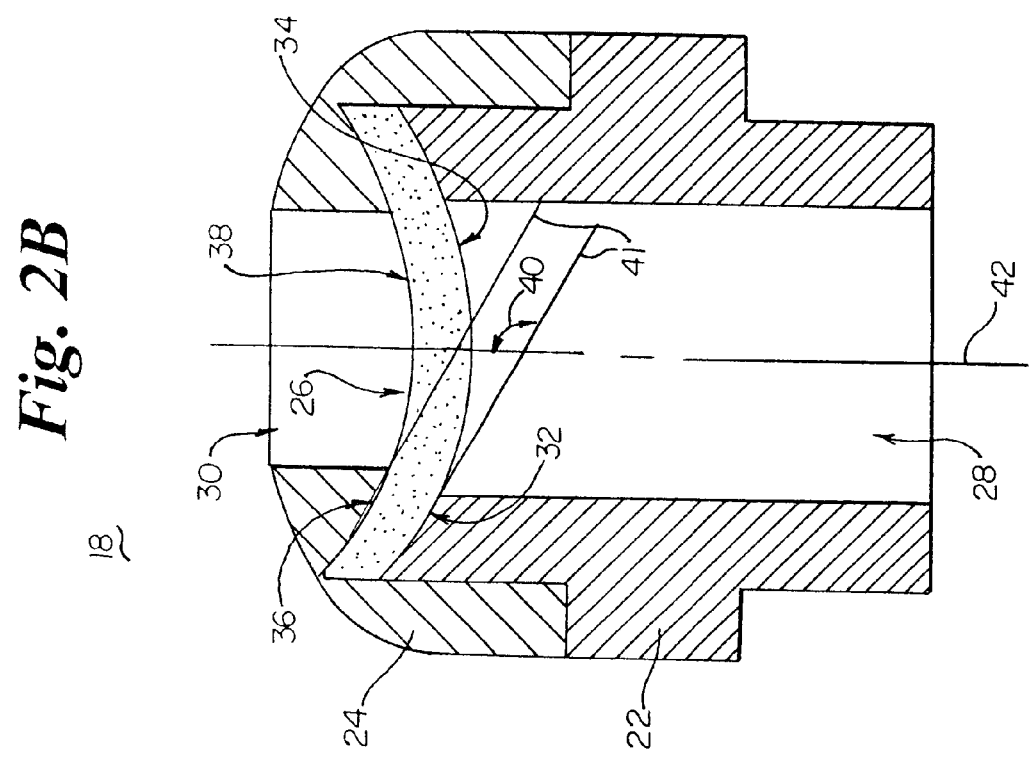
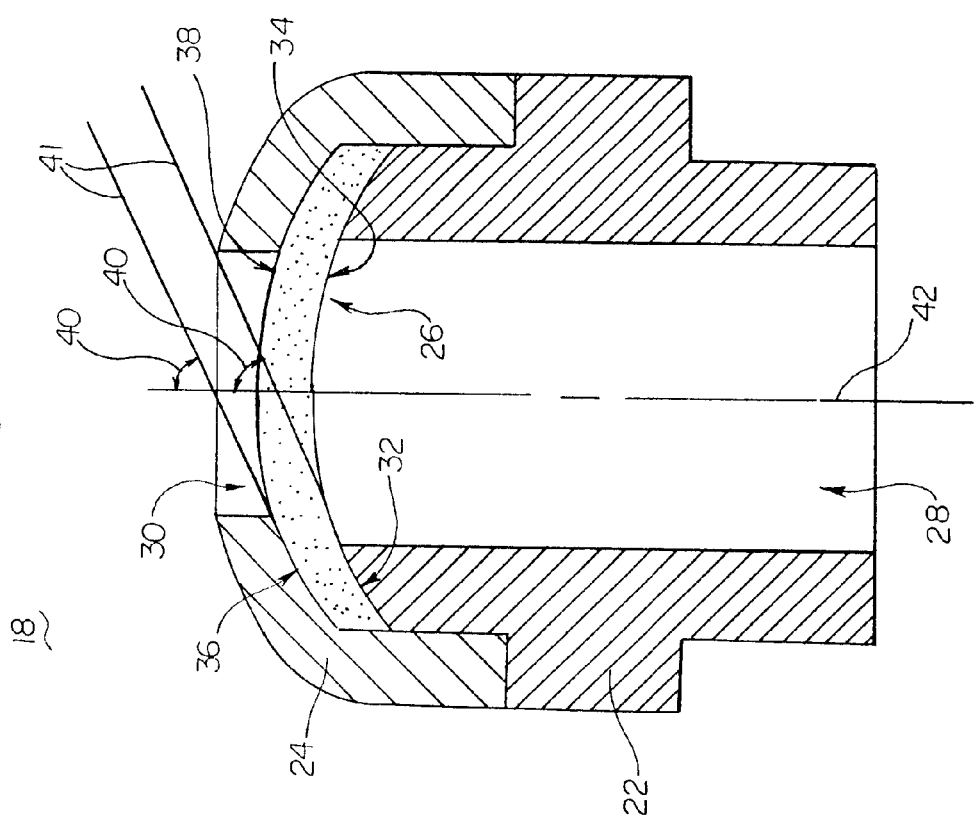

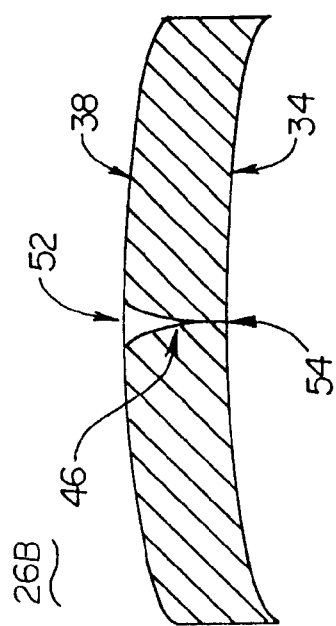
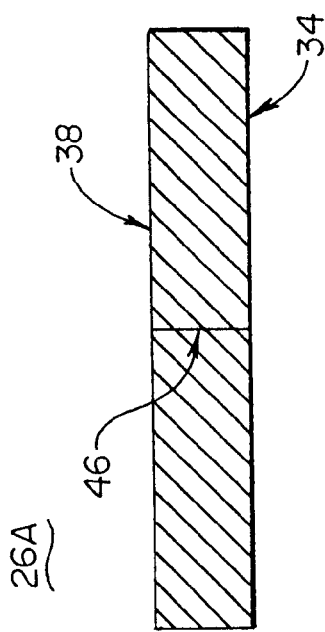

VASCULAR INTRODUCER SHEATH AND HEMOSTASIS VALVE FOR USE THEREWITH

FIELD OF THE INVENTION

The present invention generally relates to introducer sheaths for use in procedures requiring vascular access. More specifically, the present invention relates to hemostasis valves for use in such introducer sheaths.

BACKGROUND OF THE INVENTION

Vascular introducer sheaths are well known components of vascular access systems which are used in a wide variety of diagnostic and therapeutic vascular procedures, such as angiography, angioplasty, thermolysis and embolization procedures. Vascular access systems typically include an introducer sheath for use in combination with a guide wire and a dilator. The introducer sheaths usually include a hemostatic or hemostasis valve which inhibits blood loss as guide wires, catheters and the like are introduced and manipulated in the vasculature via the sheath.

An example of a known hemostasis valve is disclosed in U.S. Pat. No. 5,520,655 to Davila et al. Davila '655 discloses a hemostasis valve including an inner housing, an end cap and a valve partition disposed between the inner housing and the end cap. The end cap includes a compression ring having a diameter which is less than the diameter of the valve partition but greater than the diameter of the aperture in the end cap and the bore in the inner housing. With this arrangement, the compression ring causes the valve partition to bow outwardly. Purportedly, the bowing enhances the sealing of the slit in the valve partition. However, the compression ring creates stress concentration points on the valve partition that may compromise the integrity of the valve partition. Furthermore, an excessive amount of compression must be applied by the compression ring against the valve partition to impart the bowing effect.

A similar hemostasis valve is disclosed in International Patent Publication No. WO 99/06099 to Paul. Paul '099 discloses a hemostatic valve including a gasket seal contained in a valve body and compressed therein by a cap connected to the valve body. The valve body includes a valve seat, which in turn includes a flange and a series of annular recessed steps. The flange serves to impart a concave shape to the gasket seal. The series of annular steps serve to prevent the gasket seal from being displaced. As with the hemostasis valve disclosed in Davila '655, the hemostasis valve disclosed in Paul '099 suffers from the creation of stress concentration points imparted by the flange onto the valve gasket. The annular steps recessed in the valve body, depending on the size, may also create stress concentration points on the gasket seal. These stress concentration points may compromise the integrity of the gasket seal and also require an excessive amount of compression to impart the desired curved shape of the gasket seal.

SUMMARY OF THE INVENTION

The present invention overcomes these disadvantages by providing, in an exemplary embodiment, a vascular introducer sheath for use with a vascular access system. The vascular introducer sheath includes a tubular shaft and a hemostasis valve assembly connected to the proximal end of the tubular shaft. The hemostasis valve assembly includes a hub, a cap and a gasket disposed therebetween. The gasket may be normally-flat and may have at least one normally-closed slit extending therethrough.

Both the hub and the cap include continuous contact surfaces facing the top and bottom surfaces of the gasket. The continuous contact surfaces may be flat or gently curved, and may be smooth or include a means to grip the gasket. At least one of the contact surfaces forms a non-orthogonal angle with the longitudinal axis of the assembly to cause the gasket to become curved in response to compression between the hub and the cap. The continuous contact surfaces uniformly distribute forces onto the perimeter of the gasket to avoid stress concentration points that may compromise gasket integrity. In addition, the continuous contact surfaces increase the contact surface area and thereby reduce the amount of pressure necessary to impart the desired curved shape of the gasket.

BRIEF DESCRIPTION OF THE DRAWINGS

FIG. 1 is a plan view of a vascular access system of the present invention including an introducer sheath and a dilator;

FIGS. 2A and 2B are cross-sectional side views of hemostasis valve assemblies of the present invention for use with the introducer sheath illustrated in FIG. 1;

FIGS. 6A and 6B are a cross-sectional views of the gasket illustrated in FIG. 5, shown in the normal (relaxed) state and the curved (compressed) state, respectively.

DETAILED DESCRIPTION OF THE INVENTION

Figure 3:
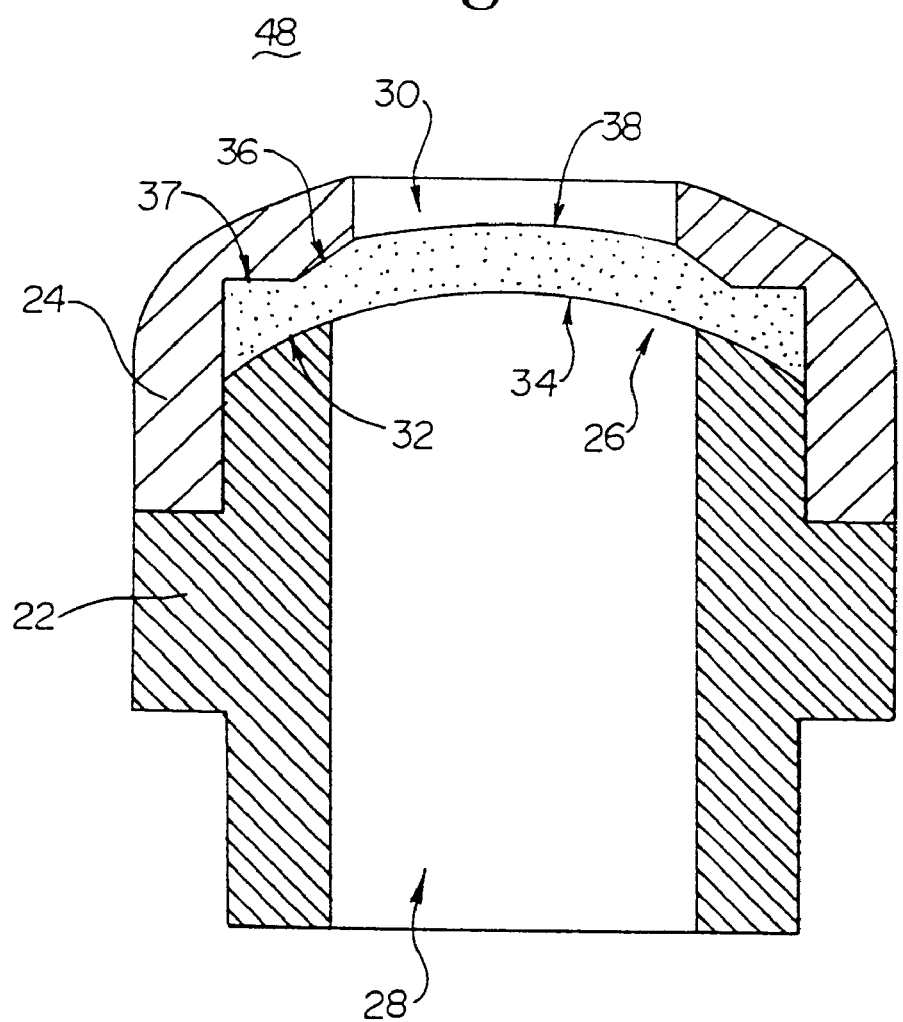
FIG. 3 is a cross-sectional side view of an alternative hemostasis valve assembly of the present invention for use with the introducer sheath illustrated in FIG. 1.

The following detailed description should be read with reference to the drawings in which similar elements in different drawings are numbered the same. The drawings, which are not necessarily to scale, depict illustrative embodiments and are not intended to limit the scope of the invention.

Refer now to FIG. 1 which illustrates a plan view of a vascular access system 10 in accordance with the present invention. Vascular access system 10 includes two primary components, namely an introducer sheath 12 and a dilator 14. Introducer sheath 12 includes an elongate shaft 16 and a hemostasis valve assembly 18. The hemostasis valve assembly 18 is connected to the proximal end of the shaft 16 utilizing conventional techniques. Hemostasis valve assembly 18 includes a hub, a cap and a gasket disposed therebetween as will be described in greater detail with reference to FIGS. 2–4. The hub of the hemostasis assembly 18 may include a side port 19 for connection to a flush or injection tube subassembly 20. The shaft 16 of the introducer 12 may have a size (outside diameter or profile) ranging from 4F to 9F, and a length ranging from 10 cm to 25 cm. The distal tip of the elongate shaft 16 is preferably tapered to facilitate smooth insertion into the vascular system and smooth transition to the dilator 14.

Refer now to FIGS. 2A and 2B which illustrate cross-sectional side views of hemostasis valve assemblies 18 for use with the introducer sheath 12 illustrated in FIG. 1. As mentioned previously, the hemostasis valve assembly 18 includes a hub 22, a cap 24 and a gasket 26 disposed therebetween. For purposes of simplicity and clarity, the side port 19 of the hub 22 is not illustrated. Similarly, although not illustrated for purposes of simplicity and clarity, the hub 22 and the end cap 24 include a means for compressive connection therebetween, such as a snap-fit connection or a threaded connection, both of which are well-known in the art.

The hub 22 includes an inner lumen 28 extending therethrough, and the end cap 24 includes an aperture 30 extending therethrough. The inner lumen 28 of the hub 22 is in fluid communication with the aperture 30 of the end cap 24 absent the gasket 26, which includes one or more slits (not shown) discussed in more detail with reference to FIGS. 5, 6A and 6B. The hub 22 and the end cap 24 may have conventional dimensions and may be formed of conventional materials using known manufacturing techniques.

Hub 22 includes a continuous surface 32 which is in intimate contact with the bottom surface 34 of the gasket 26. Similarly, the end cap 24 includes a continuous surface 36 in intimate contact with the top surface 38 of the gasket 26. The continuous contact surfaces 32, 36 may be flat or gently curved and may be smooth or include a means to grip the gasket as described with reference to FIGS. 3 and 4.

Both the surface 32 of the hub 22 and the surface 36 of the end cap 24 define a line 41 that is tangent to the surface. If a curved surface is used, the tangent line 41 may be taken at the cross-sectional mid-point of the curved surface. Either the tangent line 41 of surface 32 or the tangent lines 41 of both surfaces 32, 36 may be formed at an angle 40 with the longitudinal axis 42 of the assembly 18. The angle 40 is non-orthogonal (i.e. acute or obtuse) such that the gasket 26 becomes curved in response to compression between the hub 22 and the end cap 24. as seen in FIGS. 2A and 2B, the surface 32 of the hub 22 and the surface 36 of the cap 24 define a contact area with the gasket 26. The continuous contact surface 32 of the hub 22 and the continuous contact surface 36 of the cap 24 have parallel contact angles as illustrated by tangent lines 41 and angles 40, which are the same throughout the contact area of the gasket 26 with the hub 22 and the cap 24.

The continuous surfaces 32, 36, which may be flat or gently curved, uniformly distribute forces onto the bottom and top surfaces 34, 38 to avoid stress concentration points that may otherwise compromise the integrity of the gasket 26. In addition, the continuous contact surfaces 32, 36 increase the contact surface area and thereby reduce the amount of pressure between the hub 22 and the end cap 24 necessary to impart the desired curved shape of the gasket 26.

As illustrated, in FIG. 2A the continuous surfaces 32, 36 form an acute angle 40 with the longitudinal axis 42 such that the top surface 38 of the gasket 26 assumes a convex shape. Alternatively, as illustrated in FIG. 2B the continuous surfaces 32, 36 may form an obtuse angle 40 with the longitudinal axis 42 such that the top surface 38 assumes a concave shape. As mentioned previously, it is only necessary that the surface 32 of the hub 22 is formed at an angle 40 with the longitudinal axis 42 in order to impart a curve on the gasket 26. However, both the surface 32 of the hub and the surface 36 of the end cap 24 may be formed at an angle 40 to cause the gasket 26 to assume a curved shape. If both surfaces 32, 36 are formed at an angle 40, the angles are preferably the same but may be different.

Refer now to FIG. 3 which illustrates a cross-sectional side view of an alternative hemostasis valve assembly 48 for use with the introducer sheath 12 illustrated in figure 1. Except as specifically described herein, hemostasis valve assembly 48 is the same in form and function as hemostasis valve 18. In this embodiment, the end cap 24 includes a non-orthogonal continuous surface 36 as described previously, and a flat surface 37 that is orthogonal to the axis 42. By providing an orthogonal flat surface 37, the gasket 26 is less likely to be displaced from the recess formed between the hub 22 and the end cap 24. Accordingly, the combination of an orthogonal flat surface 37 and a nonorthogonal continuous surface 36 retains the gasket 26 between the hub 22 and the end cap 24 while guide wires, catheters and the like are advanced or retracted through the hemostasis valve assembly 48. In other words, the orthogonal flat surface 37 combined with the non-orthogonal flat surface 36 comprises a means to retain the gasket 26 between the hub 22 and the end cap 24.

Figure 4:
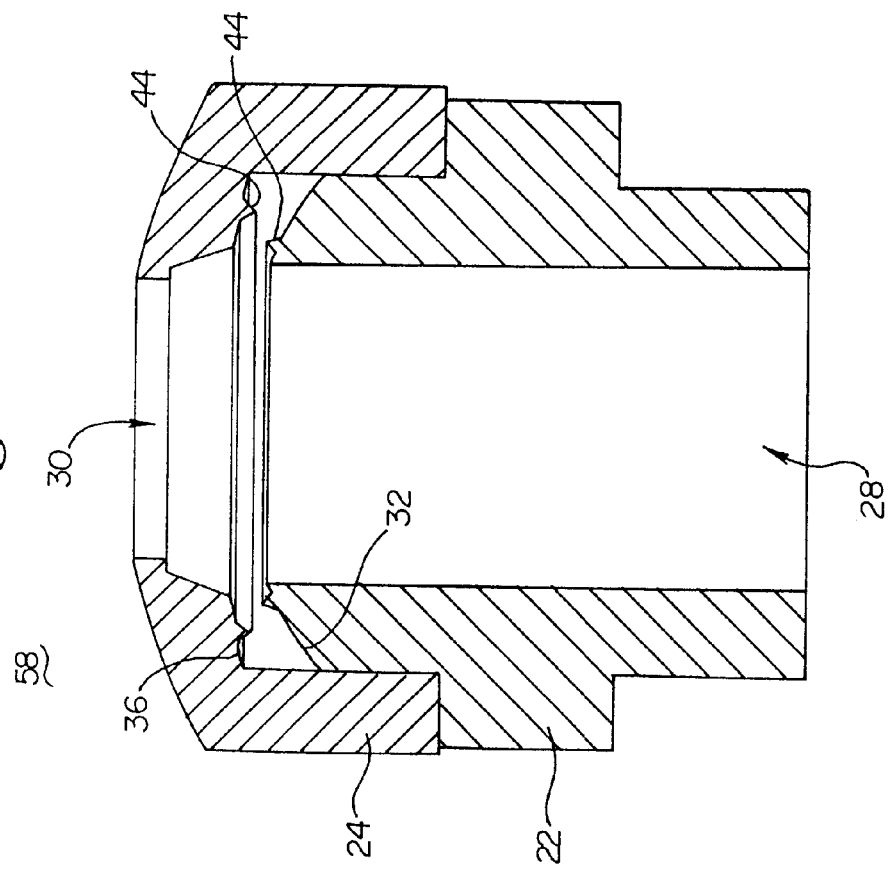
FIG. 4 is a cross-sectional side view of another alternative hemostasis valve assembly of the present invention for use with the introducer sheath illustrated in FIG. 1.

Refer now to FIG. 4 which illustrates a cross-sectional side view of another alternative hemostasis valve assembly 58 for use with the introducer sheath illustrated in FIG. 1. Except as specifically described herein, hemostasis valve 58 is the same in form and function as hemostasis valve assembly 18. For purposes of simplicity and clarity, the gasket 26 is not illustrated in FIG. 4. It should be understood, however, that the gasket 26 is disposed between the hub 22 and the end cap 24 as described previously.

In this particular embodiment, the continuous surfaces 32, 36 of the hub 22 and the end cap 24, respectively, include an annular protrusion 44 to grip the gasket 26. Annular protrusion 44 preferably has a relatively low profile of less than approximately 0.010" to minimize or avoid creating stress concentration points on the gasket 26. It is believed that the annular protrusions 44 do not contribute to curving the gasket 26, but merely retain the gasket between the hub 22 and the cap 24. Accordingly, annular protrusions 44 comprise means to retain the gasket 26 between the hub 22 and the cap 24.

Those skilled in the art will recognize that other means may be employed to grip the gasket 26. For example, a series of small knobs or ridges may be utilized. Alternatively, the contact surfaces 32, 36 may be provided with a coating having a high coefficient of friction or other roughened surface treatment. However, it is to be understood that protrusions 44 and other suitable means for gripping the gasket 26 preferably do not significantly compromise the flatness or gentle curvature of the contact surfaces 32, 36 engaging the gasket 26. These protrusions and other means to grip the gasket 26 merely increase resistance to displacement of the gasket 26 relative to the hub 22 and the end cap 24, but do not result in stress concentration or focal points that may otherwise compromise the integrity of the gasket 26.

Figure 5:
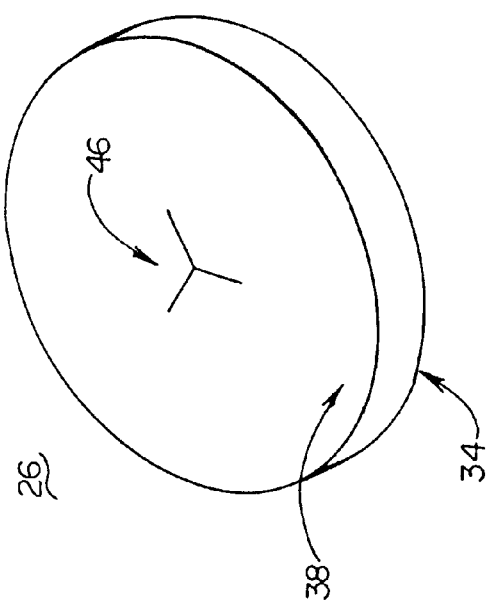
FIG. 5 is an isometric perspective view of a gasket for use with any of the hemostasis valve assemblies of FIGS. 2–4.

Refer now to FIG. 5 which illustrates an isometric perspective view of the gasket 26 for use with any of the hemostasis assemblies 18, 48, 58 illustrated in FIGS. 2–4. Gasket 26 includes a flat top surface 38 and a flat bottom surface 34 as described previously. Gasket 26 is normally flat such that the gasket 26 assumes a flat, disk shape 5 when not in compression. The gasket 26 may be formed of a variety of elastomeric materials such as PDMS, latex or other suitable material. Preferably, the gasket 26 has a durometer in the range of 15A–50A. The gasket 26 thickness may range from approximately 0.045 to 0.075 inches and may have an outside diameter ranging from 0.050 to 0.150 inches to snugly fit in the recess of the cap 24. The gasket 26 may be punched out of a sheet of elastomeric material or molded using conventional techniques. A slit 46 may be punched through the gasket 26 using a three-edged cutter or other suitable geometry, depending on the desired number and shape of the slits. Those skilled in the art will recognize that the dimensions, materials and methods of manufacture may be readily modified without departing from the scope or spirit of the invention.

Refer now to FIGS. 6A and 6B which illustrate cross-sectional views of the gasket 26 shown in the normal (relaxed) state 26A and the curved (compressed) state 26B, respectively. The normally flat gasket 26A illustrated in FIG. 6A includes a slit 46 that is normally closed. Specifically, the slit 46 is normally closed at the top surface 38 and the bottom surface 34 of the gasket 26 such that a fluid tight seal is created along the entire length of the slit 46.

Upon compression, the gasket 26B assumes a curved shape, depending on the degree of compression and the angle 40 of the contact surfaces 32, 36. For purposes of illustration only, the top surface 38 is shown to have a convex shape and the bottom surface 34 is shown to have a concave shape. The surface that assumes the convex shape creates an opening 52 while an enhanced fluid tight seal 54 is created along the concave surface. The opening 52 on the convex surface allows for easy insertion of a guide wire, catheter or the like, particularly when incorporated onto the top surface 38 of the gasket 26. The enhanced fluid tight seal 54 on the concave surface inhibits the egress of blood through the gasket 26.

The size of the opening 52 and the amount of compression at the seal 54 depends in part on the degree of curvature of the gasket 26. The curvature of the gasket 26 may be adjusted by changing the angle 40 or the amount of compression to impart the desired size of the opening 52 and the desired tightness of the seal 54. Thus, the amount of curvature may be adjusted to affect device performance in terms of hemostasis (i.e., seal) and resistance (i.e., drag) to movement of devices passing therethrough.

From the foregoing, those skilled in the art will recognize that an improved vascular introducer sheath, and in particular an improved hemostasis valve assembly has been described. The improved hemostasis valve assemblies provide continuous (e.g., flat or gently curved) contact surfaces between the gasket and the housing components (i.e., the hub and end cap). The continuous contact surfaces distribute forces uniformly onto the perimeter of the gasket to avoid stress concentration points that may otherwise compromise gasket integrity. In addition, the continuous contact surfaces increase the amount of contact area and thereby reduce the amount of pressure necessary to impart the desired curved shape of the gasket.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A vascular introducer sheath for use with a vascular access system, the vascular introducer sheath comprising:
   a tubular shaft having a proximal end and a distal end; and
   a hemostasis valve assembly connected to the proximal end of the tubular shaft, the hemostasis valve assembly including a hub having a longitudinal axis and a continuous contact surface, a cap having a continuous contact surface, and a gasket disposed therebetween defining a contact area with the hub and the cap, wherein at least one of the contact surfaces forms a non-orthogonal angle with longitudinal axis to cause the gasket to become curved in response to compression between the hub and the cap and wherein the continuous contact surface of the hub and the continuous contact surface of the cap have parallel contact anglesin cross-section which are the same throughout the contact area of the gasket with the hub and the cap to uniformly distribute forces onto the gasket and to avoid stress concentration points.

2. A vascular introducer sheath as in claim 1, wherein both contact surfaces form a non-orthogonal angle with longitudinal axis to cause the gasket to become curved in response to compression between the hub and the cap.

3. A vascular introducer sheath as in claim 2, wherein the non-orthogonal angle is acute.

4. A vascular introducer sheath as in claim 3, wherein a top surface of the gasket is convex.

5. A vascular introducer sheath as in claim 2, wherein the non-orthogonal angle is obtuse.

6. A vascular introducer sheath as in claim 5, wherein a top surface of the gasket is concave.

7. A vascular introducer sheath as in claim 1, wherein the gasket is normally-flat.

8. A vascular introducer sheath as in claim 7, wherein the gasket has at least one slit extending therethrough, the slit being normally-closed when the gasket is flat.

9. A vascular introducer sheath as in claim 1, wherein at least one of the contact surfaces includes a means to retain the gasket between the hub and cap.

10. A vascular introducer sheath as in claim 9, wherein the retaining means comprises an orthogonal flat surface.

11. A vascular introducer sheath as in claim 1, wherein the continuous contact surface of the hub and the continuous contact surface of the cap are flat.

12. A vascular introducer sheath as in claim 1, wherein the continuous contact surface of the hub and the continuous contact surface of the cap are gently curved.

13. A hemostasis valve assembly for use with a vascular introducer sheath, the hemostasis valve assembly comprising:
   a hub having a continuous contact surface and a longitudinal axis;
   a cap co-axially disposed about the hub, the cap having a continuous contact surface; and
   a gasket disposed between the hub and cap defining a contact area with the hub and the cap, the gasket having a top surface and a bottom surface, the top surface disposed adjacent the contact surface of the cap and the bottom surface disposed adjacent the contact surface of the hub, wherein the contact surface of the hub forms a non-orthogonal angle with longitudinal axis to cause the gasket to become curved in response to compression between the hub and the cap, and wherein the continuous contact surface of the hub and the continuous contact surface of the cap have parallel contact angles in cross-section which are the same throughout the contact area of the gasket with the hub and the cap to uniformly distribute forces onto the gasket and to avoid stress concentration points.

14. A hemostasis valve assembly as in claim 13, wherein the gasket is normally-flat.

15. A hemostasis valve assembly as in claim 14, wherein the gasket has at least one slit extending from the top surface to the bottom surface, the at least one slit being normally-closed at both the top and bottom surfaces when the gasket is flat.

16. A vascular introducer sheath as in claim 13, wherein at least one of the contact surfaces includes a means to retain the gasket between the hub and cap.

17. A vascular introducer sheath as in claim 16, wherein the retaining means comprises an orthogonal flat surface.

18. A hemostasis valve assembly as in claim 13, wherein the continuous contact surface of the hub and the continuous contact surface of the a are flat.

19. A hemostasis valve assembly as in claim 13, wherein the continuous contact surface of the hub and the continuous contact surface of the cap are gently curved.

20. A hemostasis valve assembly as in claim 13, wherein the contact surface of the hub forms an acute angle with longitudinal axis to cause the top surface of the gasket to become convex in response to compression between the hub and the cap.

21. A hemostasis valve assembly as in claim 13, wherein the contact surface of the hub forms an obtuse angle with longitudinal axis to cause the top surface of the gasket to become concave in response to compression between the hub and the cap.

22. A hemostasis valve assembly as in claim 13, wherein both contact surfaces form a non-orthogonal angle with longitudinal axis to cause the gasket to become curved in response to compression between the hub and the cap.

* * * * *

UNITED STATES PATENT AND TRADEMARK OFFICE
CERTIFICATE OF CORRECTION

PATENT NO. : 6,322,541 B2
DATED : November 27, 2001
INVENTOR(S) : Ronald L. West et al.

It is certified that error appears in the above-identified patent and that said Letters Patent is hereby corrected as shown below:

Column 7,
Line 15, delete "a" and insert -- cap --.

Signed and Sealed this

Third Day of September, 2002

Attest:

Attesting Officer

JAMES E. ROGAN
Director of the United States Patent and Trademark Office